(12) United States Patent
Mohseni et al.

(10) Patent No.: US 7,544,367 B2
(45) Date of Patent: Jun. 9, 2009

(54) CHEMICAL METHOD OF MAKING A SUSPENSION, EMULSION OR DISPERSION OF PYRITHIONE PARTICLES

(75) Inventors: Saeed M. Mohseni, Cromwell, CT (US); Charles W. Kaufman, Rochester, NY (US); David C. Beaty, Bergen, NY (US); John J. Jardas, Rochester, NY (US); George Polson, Harwinton, CT (US)

(73) Assignee: Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 10/176,185

(22) Filed: Jun. 20, 2002

(65) Prior Publication Data

US 2002/0197283 A1 Dec. 26, 2002

Related U.S. Application Data

(62) Division of application No. 09/512,920, filed on Feb. 25, 2000, now Pat. No. 6,432,432.

(60) Provisional application No. 60/123,066, filed on Mar. 5, 1999.

(51) Int. Cl.
*A01N 25/12* (2006.01)
(52) U.S. Cl. .............. 424/409; 424/46; 424/70.1; 424/400; 424/401; 424/405; 424/489; 514/185; 514/186; 514/188; 514/345; 514/960; 514/970; 977/23
(58) Field of Classification Search ........... 424/405, 424/400, 401, 489, 409, 421, 70.1, 641; 514/185, 514/186, 188, 345
See application file for complete search history.

(56) References Cited

U.S. PATENT DOCUMENTS

| | | | |
|---|---|---|---|
| 1,734,975 A | 11/1929 | Loomis et al. | 516/38 |
| 2,407,462 A | 9/1946 | Whiteley | 516/79 |
| 3,940,482 A | 2/1976 | Grand | 514/188 |
| 4,832,950 A | 5/1989 | Takaya et al. | 514/188 |
| 5,104,645 A | 4/1992 | Cardin et al. | 514/345 |
| 5,518,774 A * | 5/1996 | Kappock et al. | 427/384 |
| 5,540,860 A | 7/1996 | Hosseini et al. | 252/308 |
| 6,017,936 A | 1/2000 | Polson et al. | 514/345 |

FOREIGN PATENT DOCUMENTS

| | | |
|---|---|---|
| EP | 0034385 A | 8/1981 |
| EP | 0093541 A | 11/1983 |
| EP | 0173259 | 3/1986 |
| EP | 0352885 | 1/1990 |
| JP | A-60-016973 | 1/1985 |
| JP | A-08-048606 | 2/1996 |
| JP | A-08-059404 | 3/1996 |
| WO | WO 97/03637 | 2/1997 |
| WO | WO 98/41505 | 9/1998 |
| WO | WO98/41515 A | 9/1998 |
| WO | WO98/47372 A | 10/1998 |
| WO | WO98/48629 A | 11/1998 |
| WO | WO99/42210 A | 8/1999 |

* cited by examiner

*Primary Examiner*—Neil Levy
(74) *Attorney, Agent, or Firm*—Dale L. Carlson; Wanli Wu; Wiggin and Dana, LLP

(57) ABSTRACT

A method for producing a suspension, emulsion or dispersion of de-agglomerated particles (advantageously submicron-sized particles) of pyrithione salts comprising contacting agglomerated pyrithione salt particles with a de-agglomerating agent to produce the desired de-agglomerated pyrithione salt particles. Also disclosed is a method for making de-agglomerated submicron-sized particles of pyrithione salts comprision a heating step. Also disclosed are the particles made by the above methods and compositions comprising the particles and a base medium.

6 Claims, No Drawings

CHEMICAL METHOD OF MAKING A SUSPENSION, EMULSION OR DISPERSION OF PYRITHIONE PARTICLES

CROSS-REFERENCE TO RELATED APPLICATION

This application is a division of U.S. patent application Ser. No. 09/512,920, filed Feb. 25, 2000, now U.S. Pat. No. 6,432,432, which issued on Aug. 13, 2002, which claims the benefit of U.S. Provisional Application No. 60/123.066, filed on Mar. 5, 1999, the disclosures of both applications are incorporated by references in their entireties herein.

BACKGROUND OF THE INVENTION

1. Field of the Invention

The present invention relates generally to methods for preparing particles (advantageously submicron-sized particles) of pyrithione salts, and, more specifically, to methods of preparing such particles using de-agglomeration procedures subsequent to production of the particles. The present invention also relates to products made with these particles.

2. Description of the Related Art

Polyvalent metal salts of pyrithione (also known as 1-hydroxy-2-pyridinethione; 2-pyridinethiol-1-oxide; 2-pyridinethione; 2-mercaptopyridine-N-oxide; pyridinethione; and pyridinethione-N-oxide) are known to be effective biocidal agents, and are widely used as fungicides and bactericides in paints and personal care products such as anti-dandruff shampoos. The polyvalent metal salts of pyrithione are only sparingly soluble in water and include magnesium pyrithione, barium pyrithione, bismuth pyrithione, strontium pyrithione, copper pyrithione, zinc pyrithione, cadmium pyrithione, and zirconium pyrithione. The most widely used divalent pyrithione salts are zinc pyrithione and copper pyrithione.

Zinc and copper pyrithione are useful as antimicrobial agents and are active against gram-positive and negative bacteria, fungi, and yeasts. Zinc pyrithione is used as an antidandruff component in shampoos, while technical suspensions of zinc pyrithione and/or copper pyrithione are used as preservatives in paints and polymers. Synthesis of polyvalent pyrithione salts are described in U.S. Pat. No. 2,809,971 to Berstein et al. Other patents disclosing similar compounds and processes for making them include U.S. Pat. Nos. 2,786,847; 3,589,999; 3,590,035; 3,773,770.

Known methods for producing insoluble polyvalent salts of pyrithione result in platelet-shaped (or other irregular shaped) particles having an average size greater than 1 micrometer ($\mu m$), and more frequently in the range of 3 to 5 $\mu m$. These particles are either used directly, or can be converted into smaller particles. Smaller particles of pyrithione salts (i.e., less than 1 micrometer or "submicron") are often desired because they more easily form suspensions, emulsions, or dispersions, and provide a larger surface area for enhanced biocidal activity. In addition, smaller particles, particularly in the low submicron range (e.g., below about 0.2 $\mu m$ are believed to be semi-transparent to light, and below 0.1 $\mu m$ will be transparent to light). This transparency provides the opportunity to manufacture "clear" products, such as clear shampoos and soaps, that are popular in the marketplace today, while providing the larger surface area desired for enhanced biocidal efficacy.

Submicron-sized particles of pyrithione salts are usually generated by a separate mechanical manipulation step (e.g., grinding or crushing) of larger particles or crystals that are made by conventional processes. For example, European Patent Application No. 70046 describes a process for the preparation of zinc pyrithione using organic solvents. This process results in production of large crystals of zinc pyrithione. A separate, optional grinding step is used to grind the large crystals and produce zinc pyrithione particles of smaller size. In another example, U.S. Pat. No. 4,670,430 describes a process of making zinc pyrithione particles with a median size of about 0.2 $\mu m$ or less by mechanical grinding of larger particles of zinc pyrithione to the desired submicron size. Unfortunately, mechanical grinding of large pyrithione particles into a submicron sized pyrithione particles tends to not produce submicron-sized particles having a desired uniform size, shape and narrow particle size distribution. Such desired parameters are important since they are useful in rendering the behavior of the particles in consumer products, such as shampoos and coatings, predictable. In addition, grinding generally results in substantial loss of useful product and is costly in terms of the equipment, time, and energy required to provide the ground particles. Moreover, a desired particle shape for pyrithione particles, such as rods, needles, or other shapes with potentially enhanced biocidal activity, cannot easily be selected and produced by using grinding methodology.

Submicron-sized particles of pyrithione salts made by the methods of the prior art also suffer from severe agglomeration in which many of the submicron-sized particles bond together through noncovalent interactions to form larger particles of greater than 1 micron in size. Due to high mass, these large agglomerated particles tend to settle out of most consumer products over time and result in a hard packed layer of pyrithione salt that is difficult to re-disperse.

What is needed in the art is a method for producing non-agglomerated or de-agglomerated particles, advantageously having a submicron size or larger, of pyrithione salts possessing a uniform size, shape and/or size distribution. Desirably, the particles, incorporated into a solution, suspension or dispersion, are stable against settling out or agglomerate over time during shipping or storage prior to use. In addition, it is desired that the particles do not exhibit the damage that is typically associated with mechanical grinding. The present invention is believed to provide answers to these needs.

SUMMARY OF THE INVENTION

In one aspect, the present invention relates to a method for producing a suspension, emulsion, or dispersion of de-agglomerated (advantageously submicron-sized) particles of pyrithione salts, comprising contacting agglomerated pyrithione salt particles with an de-agglomerating agent, optionally in the presence of sonic energy, to produce said suspension, emulsion, or dispersion of de-agglomerated particles of pyrithione salts.

In another aspect, the present invention provides a method for making de-agglomerated submicron-sized particles of pyrithione salts comprising the steps of:

a) filtering large particles of pyrithione salts having a particle size in a range of from 1 to 50 microns to provide filtered particles, b) contacting the filtered particles with at least one de-agglomerating agent selected from the group consisting of electrolytes, surfactants, dispersants, and combinations thereof, to provide a suspension or dispersion of de-agglomerated particles, and c) heating said de-agglomerated particles to an elevated temperature of at least 60 degrees Centigrade in order to cause a reduction in the size of the de-agglomerated particles to a submicron size, thereby producing said de-agglomerated submicron-sized particles of pyrithione salts.

In yet another aspect, the present invention relates to a suspension, emulsion, or dispersion of de-agglomerated pyrithione particles made by the above methods.

In yet another aspect, the present invention relates to a personal care composition comprising at least one component selected from the group consisting of shampoo, soap, skin care medicament, and combinations thereof, and additionally comprising an antimicrobially effective amount of de-agglomerated particles made by any of the above methods.

These and other aspects will become apparent upon reading the following detailed description of the invention.

DETAILED DESCRIPTION OF THE INVENTION

It now has been surprisingly found, in accordance with the present invention, that a solution is provided to the problem of producing dispersions of nonagglomerated (advantageously submicron-sized) particles of pyrithione salts. The present inventors have solved this problem by treating particles of pyrithione salts made in a conventional manner with a deagglomerating agent that disperses agglomerated pyrithione salt particles and forms a uniform dispersion of submicron-sized particles of pyrithione salts that do not settle out over time. De-agglomerated particles produced in accordance with the method of the present invention also display a narrow size distribution that make them ideal for use in many consumer products, such as shampoos, coatings, and the like.

The present inventors have unexpectedly discovered that agglomerated particles of pyrithione salts result in part from non-covalent molecular interactions, such as ionic attraction between small particles, and that these non-covalent interactions can be neutralized by treating agglomerated particles made by prior art methods with a de-agglomerating agent. For purposes of the present invention, the de-agglomerating agent may be a surfactant, an electrolyte, a dispersant, or a combination of these. The method of the present invention produces a dispersion, suspension or emulsion comprising particles of pyrithione salts and having numerous advantages when incorporated into personal care products, such as antidandruff shampoos, soaps, and the like. For example, a dispersion of submicron-sized pyrithione salt particles possesses enhanced biocidal activity, relative to such particles having a larger size, due to an increased surface area per unit volume. In addition, the submicron-sized particles that are suitably generated according to the method of the present invention do not re-agglomerate and remain homogeneously dispersed in solution. Prevention of re-agglomeration of the particles is particularly important in the production of personal care products because agglomerated particles, or those that are prone to agglomerate, tend to settle out over time and produce a dense layer of particles on the bottom of containers resulting in an unappealing product having limited utility.

The present inventors have also surprisingly discovered that application of heat (at a temperature s of at least 60 degrees Centigrade) to needle shaped pyrithione salt particles having particle sizes in the range of 1-50 microns causes the particles to decrease in size to the submicron range. This finding is particularly advantageous since the needles are easily filtered to remove impurities, whereas submicron-sized pyrithione salt particles are difficult to filter. Therefore, filtration of the needles, followed by de-agglomeration of the needles, and heating to produce the desired purified, submicron-sized particles should prove fruitful to the pyrithione salts manufacturing community.

As used herein, the term "submicron-sized particles" refers to particles having an average diameter of less than one micron. The term "suspension, emulsion, or dispersion" is refers to a homogeneous solution of particles that do not settle out or precipitate over time. The term "agglomerated pyrithione salt particles" refers to particles of pyrithione salts that are bound together by non-covalent forces, such as ionic interactions. The term "deagglomerated particles" refers to particles that are not bonded together by non-covalent forces. The term "de-agglomerating agent" refers to any agent that neutralizes or reduces the non-covalent forces in agglomerated particles.

The term "sonic energy" is broadly defined to encompass sound waves in the audio sound spectrum, infrasound spectrum, and ultrasound spectrum, preferably in the frequency range of from 20 Hz to 900,000 Hz (900 kHz) with power levels in the range from about 20 to about 5000 watts, more preferably 100 to 1000 watts, most preferably 250 to 750 watts, and is decibel (dB) levels from about 10 dB to about 180 dB, preferably 50 to 100 dB, most preferably 65 to 85 dB. The term "sonication", as used herein, refers to application of sonic energy.

As used herein, the term "water-soluble salts of pyrithione" or "water-soluble pyrithione salts" include those salts of pyrithione in which the hydrogen atom of the thiol group is substituted with a monovalent cation. The term "water-soluble polyvalent metal salt" refers to those water-soluble salts in which the cation has a charge of +2 or greater. The terms "particles of pyrithione salts" or "pyrithione salt particles" as used herein refer to those salts of pyrithione that form precipitates and are essentially insoluble or sparingly soluble in the surrounding medium. The term "dispersant" as used herein refers to a compound that promotes uniform and maximum separation of extremely fine solid particles (i.e., colloidal size), and that does not promote foaming.

An aspect of the present invention relates to a method for treating agglomerated pyrithione salt particles made according to known methods with a de-agglomerating agent to produce a suspension, emulsion, or dispersion of particles (advantageously submicron-sized) particles of pyrithione salts.

Pyrithione salt particles may be made by any process known in the art. In one embodiment, pyrithione or a water-soluble salt of pyrithione is reacted with a water-soluble salt of a selected polyvalent metal in the presence of a dispersant to form pyrithione salt particles as a precipitate. Pyrithione in its acid form, or a water-soluble salt of pyrithione may be used in the reaction. Useful water soluble salts of pyrithione preferably include an ammonium ion or an alkali metal ion such as sodium. Accordingly, exemplary water soluble salts of pyrithione include sodium pyrithione, potassium pyrithione, lithium pyrithione, ammonium pyrithione, and combinations of these. The most preferred water-soluble salt of pyrithione useful in the present invention is the sodium salt (i.e., sodium pyrithione). The amount of pyrithione or water-soluble salt of pyrithione can vary over a wide range and establishing a useful amount is within the capabilities of the ordinary skilled practitioner based on the stoichiometry of the reaction and the required amount of particles that must be generated. A preferred amount of pyrithione or water-soluble pyrithione salt is from about 3% to about 52% by weight of the total weight of the reaction mixture.

Exemplary water-soluble polyvalent metal salts useful in accordance with the method of the invention include example zinc salts, tin salts, cadmium salts, copper salts, silver salts, zirconium salts, magnesium salts, aluminum salts, and the like. Combinations of these salts may also be employed.

Useful counterions for these metals include nitrates, acetates, sulfates, halides or combinations thereof. Preferred water-soluble polyvalent metal salts include zinc chloride ($ZnCl_2$), copper chloride ($CuCl_2$), zinc acetate ($Zn(O_2CCH_3)_2$) and zinc sulfate ($ZnSO_4$). The amount of water-soluble polyvalent metal salt can vary depending on the amount of water-soluble salt of pyrithione. The molar ratio of pyrithione or water-soluble salt of pyrithione to the water-soluble polyvalent metal salt is generally in the range from about 1:2 to about 1:8. Preferably, a slight stoichiometric excess (e.g., 5% of water-soluble polyvalent metal salt by weight over pyrithione or water-soluble salt of pyrithione) is desirable to ensure a complete reaction.

Useful media or carriers for the reaction include aqueous media such as water, or water in combination with one or more organic solvent(s). Useful organic solvents include alcohols, such as methanol, ethanol, amines such as diethanolamine, ether, esters, and the like.

Optional ingredients such as dispersants, surfactants, pearlizing agents (e.g., $TiO_2$-coated mica), and the like, may also be included in the reaction mixture singly or in any combination. Exemplary dispersants include salts of polymerized alkyl naphthalene sulfonic acids, such as "DARVAN 1" (sodium naphthalene sulfonic acid formaldehyde, a product of R.T. Vanderbilt Co. Inc.), "DEMOL N" (sodium salt of naphthalene sulfonic acid, a product of Kao Chemicals), "DAXAD 11" (sodium salt of polymerized alkyl naphthalene sulfonic acids, a product of W.R. Grace & Co.), "TAMOL N" (sodium salt of condensed naphthalene sulfonic acid, a product of Rohm and Haas Co.), "HAROL KG" (potassium salts of polymerized alkyl naphthalene sulfonic acids, a product of Graden Chemical Co.), "HAROL RG-71" (sodium salts of polymerized alkyl naphthalene sulfonic acids, a product of Graden Chemical Co.), "LOMAR LS" (sodium salt of condensed mononaphthalene sulfonic acid, a product of Henkel Corp.) and the like.

Exemplary surfactants include nonionics, anionics, cationics, and amphoterics (the latter being also commonly referred to as "zwitterionics"). Nonionic surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, alkyl sulfonates, and the like. Illustrative cationic surfactants include alkyl triammonium halide, non-linear alkyl dimethyl halide, alkyl dimethyl benzyl ammonium halide-containing surfactants, and the like. Illustrative amphoteric surfactants include polyglycol ether derivatives, ethoxylate oxazoline derivatives, lauramidopropyl betaine, lecithin, and the like.

Generally, these ingredients are utilized in the methods of the present invention in a pyrithione salt-dispersing effective amount, preferably an amount of from about 0.1 to about 20% by weight, more preferably from about 0.1 to about 5% by weight, and most preferably from about 0.1 to about 6% by weight, all based on the total weight of the reaction mixture.

The temperature of the reaction may be any temperature which permits precipitation of particles of pyrithione salt. Preferable temperatures for the reaction are in the range of from between about 4 and about 100° C., more preferably between about 25 and about 68° C., and most preferably between about 30° C. and about 350° C.

In addition, the reaction may be gently agitated to promote formation of the particles. Generally, gently stirring the reaction at 150 rpm or less, and preferably about 100 rpm, after all the ingredients have been combined is sufficient to promote formation of the particles.

Additional inorganic salts, such as potassium chloride, sodium chloride, magnesium chloride, the corresponding sulfates, citrates, nitrates, and the like, may be added to the reaction medium to control particle length and shape. For example, suitable addition of salts can result in particles of pyrithione salts having a variety of advantageous shapes, including nonspherical or non-platelet form, such as rods, needles, cylinders, cones, ellipsoids, prisms, parallelepipeds, pyramids, and the like. The particles formed by the present invention may also take the form of tetrahedrons, hexahedrons (cube), octahedrons, dodecahedrons, icosahedrons, and the like. The present inventors have observed that certain shapes of pyrithione salt particles offer advantages of increase biocidal activity due to increased surface area.

Preferably, the additional salts are included in the reaction mixture from 0.1% by weight to about 10% by weight, more preferably from about 1% by weight to about 8% by weight, and most preferably from about 3% by weight to about 6% by weight, all based on the total weight of the reaction mixture.

A particularly useful amount of additional sodium chloride added to the reaction mixture to control particle size and shape is 5% by weight based on the total weight of the reaction mixture.

In one order to produce the elongated particles of the invention, pyrithione or a selected water-soluble salt of pyrithione and a selected water-soluble polyvalent metal salt are reacted in the presence of a surfactant or combination of surfactants in any suitable reaction vessel at a temperature below 70° C., and preferably between about 10° C. and 68° C. In a preferred embodiment, sodium pyrithione is reacted with zinc chloride or zinc sulfate in the presence of salt (e.g., sodium chloride) and a selected surfactant or combination of selected surfactants at about 35° C. to form zinc pyrithione having rod or needles shapes, along with aqueous sodium chloride or aqueous sodium sulfate as by-products. The particles may also be utilized in a "continuous" process in which the zinc pyrithione particles are collected, and the mother liquor containing aqueous sodium chloride or sodium sulfate is recycled back to the reaction vessel to provide a source of additional salt. An optional filter (e.g., carbon or charcoal filter) may be employed to remove impurities such as colored organic compounds from the mother liquor. Particles of zinc pyrithione so formed have a "needle" or "rod" appearance. Generally, the rods or needles of zinc pyrithione salt produced in accordance with the present invention are between about 0.1 and about 1 μm in width and between about 2 and about 50 μm in length. Accordingly, the aspect ratio of the elongated particles is greater than about 1, and more preferably from about 2 to about 500.

The pyrithione salt particles may be isolated from the mother liquor by filtration, centrifugation, sedimentation, or other isolation methods known in the art. Subsequent procedures, such as grinding, may also be performed. Alternatively, the agglomerated particles in the reaction medium may be treated with a deagglomerating agent directly.

During particle formation, either by the above exemplary method or by other methods known in the art, the individual pyrithione salt particles aggregate into larger agglomerates having sizes greater than about 1 micron. To reduce or eliminate this aggregation and to obtain a population of individual particles having sizes of less than 1 micron, the aggregated particles are treated with a deaglommerating agent to produce a dispersion of submicron-sized particles of pyrithione salts.

The deagglomerating agent used in the method of the present invention may be any agent that separates agglomerated particles of pyrithione salt. Examples of such deagglomerating agents include electrolytes, surfactants, sonic energy, and combinations of these. The inventors have unexpectedly found that treatment of agglomerated particles with a deagglomerating agent neutralizes the noncovalent forces that result in agglomeration of the particles, and results in production of a population of pyrithione salt particles having sizes of less than 1 micron.

Electrolytes used as a deagglomerating agent in the method of the present invention include alkali metal or alkaline earth metal salts (e.g., alkali metal or alkaline earth metal salts of chloride, sulfate, carbonate, citrate, benzoate), alkali metal or alkaline earth metal oxides, alkali metal or alkaline earth metal hydroxides, and combinations thereof. Particularly useful electrolytes include sodium chloride, calcium chloride, zince chloride, sodium oxide, calcium oxide, zinc oxide, sodium hydroxide, calcium hydroxide, and zinc hydroxide. Combinations of two, three, four, or more, of these electrolytes may also be used in accordance with the method of the present invention.

Preferably, electrolytes used according to the method of the present invention range from about 0.01 to 10% by weight, more preferably, from about 0.1 to 5% by weight, and most preferably from about 0.5 to 3% by weight, based on the total weight containing the admixture of aggregated particles (on a dry weight basis).

Dispersants useful in the present invention include salts of polymerized or unpolymerized alkyl naphthalene sulfonic acids. Useful salts of polymerized alkyl naphthalene sulfonic acids include "DARVAN 1" (sodium naphthalene sulfonic acid formaldehyde, a product of R.T. Vanderbilt Co. Inc.), "DEMOL N" (sodium salt of naphthalene sulfonic acid, a product of Kao Chemicals), "DAXAD 11" (sodium salt of polymerized alkyl naphthalene sulfonic acids, a product of W.R. Grace & Co.), "TAMOL N" (sodium salt of condensed naphthalene sulfonic acid, a product of Rohm and Haas Co.), "HAROL KG" (potassium salts of polymerized alkyl naphthalene sulfonic acids, a product of Graden Chemical Co.), "HAROL RG71" (sodium salts of polymerized alkyl naphthalene sulfonic acids, a product of Graden Chemical Co.), "LOMAR LS" (sodium salt of condensed mononaphthalene sulfonic acid, a product of Henkel Corp.) and the like.

Surfactants used as a deagglomerating agent in the method of the present invention anionic surfactants, cationic surfactants, nonionic surfactants, amphoteric surfactants (also known as "zwitterionics"), and the like.

Useful nonionic surfactants include linear alcohol alkoxylates, such as the linear alcohol ethoxylates, ethyoxylated/propoxylated block copolymers, ethyoxylated/propoxylated fatty alcohols, and polyoxyethylene cetyl ethers, and the like. Useful linear alcohol alkoxylates are commercially available, for example, under the registered trademark POLY-TERGENT SL-42, a product of Olin Corporation. If desired, the alcohol alkoxylate is suitably end-capped with a lower alkyl group, and such a product is commercially available as POLY-TERGENT SLF-18, a propylene oxide-capped linear alcohol alkoxylate that is also a product of Olin Corporation, and these end-capped linear alcohol alkoxylates are notably low foaming during use. Also advantageous for use in accordance with the present invention are surfactants within the group commercially available as POLY-TERGENT SLF-18B series surfactants, which are surfactants characterized by enhanced biodegradability (also products of Olin Corporation), being alkene oxide-capped linear alcohol alkoxylates, containing ethylene oxide moieties in the backbone, and suitably also containing at least one propylene oxide moiety in the backbone, as disclosed, for example, in U.S. Pat. Nos. 4,925,587 and 4,898,621.

Other useful nonionic surfactants include one commercially available as NEODOL 91-6, a registered trademark surfactant product of Shell Chemical. This surfactant is a detergent range mixture of $C_9$-$C_{11}$ linear primary alcohol ethoxylates having an average of six moles of ethylene oxide per mole of alcohol. Other useful nonionic surfactants include those is containing a linear $C_9$-$C_{11}$ carbon chain and five or six ethylene oxide or propylene oxide groups per molecule.

Useful anionic surfactants include alkyl diphenylether disulfonates, alkyl phenyl ethoxylated phosphate esters, carboxylated linear alcohol alkoxylates, linear alkyl benzene sulfonic acid, diisobutyl sulfosuccinate, and alkyl sulfonates. Useful anionics also include the alkylated diphenyl oxide sulfonates, and their methods of preparation are well-known, as illustrated by the disclosures of U.S. Pat. Nos. 3,264,242; 3,634,272; and 3,945,437, the disclosures of which are all incorporated herein by reference. Commercial methods of preparation of the alkylated diphenyl oxide sulfonates generally do not produce species which are monoalkylated, monosulfonated, dialkylated or disulfonated. The commercially available species typically are predominately (greater than 90 percent) disulfonated and are a mixture of mono- and dialkylated with the percentage of dialkylation being about 15 to about 25 percent, and the percentage of monoalkylation being about 75 to 85 percent. Most typically, the commercially available species are about 80 percent is monoalkylated and 20 percent dialkylated.

Two illustrative commercially available solutions containing alkylated diphenyl oxide sulfonate surfactants are DOW-FAX 8390 and DOWFAX 8390A surfactants, trademarked products of The Dow Chemical Company. In each, the alkyl group is predominantly a hexadecyl $C_{16}$ group. These products are suitably employed in a solution fully or partially neutralized with ammonium hydroxide if desired.

An advantageous anionic surfactant is also provided by reacting the above-described alkylated diphenyl oxide sulfonates with a piperazine compound to produce a molar ratio of sulfonate compound to piperazine compound of between about 10:1 and about 1:10, preferably between about 2:1 and about 1:2. Although any piperazine compound can be used for such reaction, preferred compounds include those selected from the group consisting of 1,2-aminoethyl piperazine, 1,4-piperazinediethane sulfonic acid, anhydrous piperazine, hydrated piperazine, and combinations thereof.

Other useful anionics are polycarboxylated alcohol alkoxylates, preferably those selected from acids or organic or inorganic salts of the following: polycarboxylated linear alcohol alkoxylates, polycarboxylated branched alcohol alkoxylates, polycarboxylated cyclic alcohol alkoxylates, and combinations thereof. These polycarboxylated alcohol alkoxylates typically contain at least two succinic acid radicals per molecule. Preferred polycarboxylated alcohol alkoxylates are those having a backbone containing both poly(propylene oxide) and poly(ethylene oxide) blocks, and such preferred polycarboxylated alcohol alkoxylates are readily commercially available, for example, as POLY-TERGENT CS-1, a trademarked surfactant of Olin Corporation. If desired, at least a portion of the acid groups on the polycarboxylated alcohol alkoxylate are neutralized with a base to provide the corresponding salt. Suitable bases include alkali metal hydroxides, alkaline earth metal hydroxides, and metal-free hydroxides, including potassium hydroxide, ammonium hydroxide, calcium hydroxide, magnesium hydroxide, ammonia, mono-, di- and tri-ethanol amines, and combinations thereof. Sodium hydroxide is preferred, and although potassium hydroxide can be employed, it is not preferred. The organic or inorganic base is preferably employed in at least an equimolar amount relative to the number of moles of polycarboxylated alcohol alkoxylated used. The polycarboxylated alcohol may also contain a polycarboxylic acid, for example, polyacrylic acid, along with the starting alcohol alkoxylate and esters of the alkoxylate of the polycarboxylic acid.

Although individually the cationic and the amphoteric surfactants are acceptable for use in the process of the present invention, they may also be used in combination with at least one surfactant from one of the other classes. Illustrative cationics include alkyl triammonium halide, non-linear alkyl dimethyl halide and alkyl dimethyl benzyl ammonium halide-containing surfactants. Illustrative amphoteric surfactants include polyglycol ether derivatives, ethoxylate oxazoline derivatives, lauramidopropyl betaine, and lecithin.

Suitable blends can be employed in the process of the present invention based on various combinations of the above-described surfactants. Such a blend can be any combination of two or more surfactants, between or within the above-described four broad classes of surfactants. Combinations can include blends of: anionic with anionic, anionic with nonionic, anionic with cationic, anionic with amphoteric, cationic with cationic, cationic with amphoteric, nonionic with nonionic, nonionic with amphoteric, and amphoteric with amphoteric. Likewise, ternary and quaternary blends of surfactants by selecting three or four surfactants, respectively, from within or among the above-described classes.

Suitably, any single or combination of two, three or four surfactants from the following illustrative list are suitably employed: (a) nonionics, including alkoxylated linear alcohols (such as POLY-TERGENT SLF-18 surfactant, a product of Olin Corporation), linear alcohol ethoxylates (such as NEODOL 91-8 surfactant, a product of the Shell Corporation), ethoxylated linear alkyl benzene (such as TRITON X-100 surfactant, a product of Union Carbide Corporation), and EO/PO block copolymers (such as POLY-TERGENT E-17A surfactant, a product of Olin Corporation); (b) anionics, including alkyl diphenyl ether disulfonates (such as POLY-TERGENT 2A1 surfactant, a product of Olin Corporation), alkyl phenyl ethoxylated phosphate esters (such as Wayfos M-60 surfactant, a product of Olin Corporation), carboxylated linear alcohol alkoxylates (such as POLY-TERGENT CS-1 surfactant, a product of Olin Corporation), linear alkyl benzene sulfonic acid (such as BIOSOFT S-130 surfactant, a product of Stepan Company), alpha-olefin sulfonates (such as BIO TERG AS-40 surfactant, a product of Stepan Company), dialkylsulfosuccinates (such as AROWET SC-75 surfactant, a product of Arol Chemical Products), and alkyl sulfates (such as STEPANOL SLS surfactant, a product of Stepan Company); (c) cationics including alkyl triammonium halides (such as CTAB surfactant, a product of VWR Scientific Inc.), polyoxyethylene cocoamine (such as MAZEEN surfactant, a product of PPG Industries), primary alkyl amines (such as ARMEEN surfactant, a product of Akzo Chemical Co.), dicoco dimethyl ammonium halide (such as JET QUAT surfactant, a product of Jetco Chemical Inc.), di-isodecyl dimethyl ammonium halides (such as AMMONYX K9 surfactant, a product of Stepan Company), and diethyl aminoethyl stearate (such as CERASYNT 303 surfactant, a product of ISP Van Dyke); and, (d) amphoterics, including polyglycol ether derivatives (such as ALBEGAL A surfactant, a product of Ciba-Geigy), ethoxylated oxazolin derivatives (such as ALKATERG T-IV surfactant, a product of Angus Chemicals), lauramide propyl betain (such as LEXAINE C surfactant, a product of Inolex Chemicals), lecithin (such as CANASPERSE surfactant, a product of Can Amoral), disocium cocoamphodiacetate (such as MONATERICS surfactant, a product of Mona Industries), complex fatty amine salt (such as MAFO 13 surfactant, a product of PPG Industries), and cocoamine oxide (such as MACKAMINE CO surfactant, a product of the McIntyre Group Ltd.). Combinations of two, three, four, or more, of these surfactants may also be used in accordance with the method of the present invention.

Preferably, surfactants used according to the method of the present invention range from about 0.01 to 10% by weight, more preferably, from about 0.025 to 5% by weight, and most preferably from about 0.05 to 1% by weight, based on the total weight of the admixture containing aggregated particles (on a dry weight basis).

Sonic energy is optionally employed in the methods of the present invention in order to facilitate or expedite the desired de-agglomeration being effected by the de-agglomerating agent(s), and to enhance the uniformity of the resulting suspension, dispersion or emulsion. If used, the sonic energy is preferably applied to the agglomerated pyrithione salt particles in the presence of the de-agglomerating agent(s) to form a highly uniform suspension of non-agglomerated particles. The sonic energy preferably has a frequency of from about 20 Hz to about 900,000 Hz (900 kHz), more preferably from about 5 kHz to about 105 kHz, and most preferably from about 16 kHz to about 20 kHz. Combinations of frequencies may also be used, depending on the configuration of the particular sanction apparatus. The energy level output that results from the sonic energy applied to the reaction mixture is preferably in the range from about 20 to about 5000 Watts, more preferably from about 100 to about 1000 Watts, and most preferably from about 400 to about 600 Watts. An example of a suitable sonication device that is useful according to the method of the invention is a Nearfield NAP Model 3606 acoustical processor (available commercially from Advanced Sonic Processing Systems, Woodbury, Conn.), although any sonication device may be employed in the method of the invention.

It will be noted that the sound levels that could be produced using the levels of sonic energy discussed above can exceed 100 decibels (dB) and potentially reach levels as high as 140 dB. In order to avoid hearing impairment, proper safety and sound abatement procedures should be undertaken when decibel levels are greater than about 80 dB.

Preferably, in the batch process, sonic energy is applied to the reaction mixture through a climate probe that is placed in direct contact with the particles after their formation. Other methods of applying sonic energy are also feasible, such as a pipe which carries the sonic energy to the reaction vessel, or a chamber lined with sonic energy transducers. The latter method is particularly useful in the continuous manufacture of particles as described in copending U.S. patent application Serial No. 60/075,803, filed on Feb. 24, 1998), incorporated herein by reference in its entirety.

The uniform, well-dispersed suspension of non-agglomerated particles made according to the method of the invention is useful in the production of personal care products (e.g., shampoos, soaps, etc.), cleaning products, paints, coatings, foodstuffs, fertilizers, pool chemicals, foodstuffs, and the like. For example, deagglomerated zinc pyrithione particles made according to the method of the invention are a useful component of antimicrobial-containing shampoos, e.g., as an antidandruff additive in providing an antidandruff efficacy characteristic to shampoos. Generally, the antimicrobial-containing personal care composition of the present invention may contain any "base medium" component found in shampoos, soaps, or skin care medicaments, such as, for example, glycerine, aloe, surfactants such as dodecyl-benzene sulfonate ("DDBS"), mineral oil, water, and combinations thereof. Other such components are described in the examples provided hereinbelow.

The following examples are intended to illustrate, but in no way limit the scope of the present invention. All parts and percentages are by weight and all temperatures are in degrees Celsius unless explicitly stated otherwise. In the following Examples "q.s." means quantity sufficient, generally 0.1 to 2% by weight.

EXAMPLES

Example 1

Production of Needles of Zinc Pyrithione

To a 1200 g of 6% sodium pyrithione solution was added 6.0 g of dispersant (sodium salt of polymerized alkyl naphthalene sulfonic acid sold under the tradename DARVAN 1 available from J.T. Vanderbilt) in a 3000 ml jacketed cylindrical pyrex reactor. The temperature was raised to 35° C. and maintained throughout the reaction sequence. 437 g of a 10% aqueous zinc sulfate monohydrate solution was pumped into the reactor over 50 to 60 minutes using a peristaltic pump. The product slurry was isolated by filtration with a Buchner funnel and washed with water.

Upon analysis, the isolated reaction product was about 19.6% zinc pyrithione by weight. Under microscopic examination, the isolated product was found to consist of particles of zinc pyrithione having rod or needle shape.

Example 2

Production of Needles of Zinc Pyrithione

A solution of 355 g of 16.9% by weight sodium pyrithione, 845 ml water, and 2.4 g of DARVAN 1 (sodium naphthalene sulfonic acid formaldehyde) was placed in a 2000 ml jacketed reaction vessel and warmed to 39° C. A solution of 198.5 g of 20% by weight zinc sulfate monohydrate and 595.4 ml water was added over about 68 minutes. Following addition of the zinc sulfate solution, the mixture was stirred for 20 minutes and the product was isolated by filtration and washed. The isolated precipitate was assayed and found to contain about 33.6% by weight zinc pyrithione.

The zinc pyrithione particles were resuspended in an aqueous solution of water and DARVAN 1 (sodium naphthalene sulfonic acid formaldehyde) to form solution containing 25% by weight zinc pyrithione and 0.1% by weight DARVAN 1 dispersant. The particles were analyzed on a Horiba 910 Particle Size Analyzer. Photomicrographs showed that the particles had an elongated form and appeared as rods or needles. The width of the rods and needles varied from about 0.1 to about 1 μm, and the length of the rods and needles varied from about 2 to about 10 μm. Repeated particle size analysis of this product using the Horiba 910 Analyzer over time (i.e, during several days of measurement) indicated that the particle size distribution did not change. Hence, the agglomerates had been removed, and re-agglomeration did not reoccur.

Example 3

De-agglomeration of Agglomerated Zinc Pyrithione Particles.

1000 g of 25% aqueous solution of zinc pyrithione particles made in accordance with the protocol of Examples 1 and 2 above were poured into a 2 L beaker. 1 gram of DARVAN 1 dispersant and 1 gram of calcium chloride were added respectively to the beaker and mixed with a hand mixer for 1-2 minutes at high speed. The contents are then transferred to a 2 liter glass jacketed reactor and gently mixed at about 150 rpm using Lithinin A320 blades. The reactor was heated to about 65° C. and held for approximately 15 minutes. Chloroisothiazolone was added as a preservative to a final concentration of approximately 3 ppm during heating. Approximately 3 minutes after addition of the preservative, the heat is turned off and the mixture is allowed to cool to room temperature. The particles are then transferred to a storage container and analyzed over several days for size, dispersion, color, settlement and agglomeration. The particle size distribution did not change over a period of several days (as shown by repeated measurements of the product using a Horiba 910 Particle Size Analyzer), thus demonstrating that the particles did not re-agglomerate over time.

Example 4

Deagglomeration of Agglomerated Zinc Pyrithione Particles.

1000 g of 25% aqueous solution of zinc pyrithione particles made in Example 1 or 2 above were poured into a 2 L beaker. 0.5 gram of WITCAMIDE 5130 series surfactant, an alkanolamide nonionic surfactant of Witco Chemicals, and 10 grams of sodium chloride were added respectively to the beaker and mixed with a hand mixer for 1-2 minutes at high speed. The contents are then transferred to a 2 liter glass jacketed reactor and gently mixed at about 150 rpm using Lithinin A320 blades. The reactor was heated to about 65° C. and held for approximately 15 minutes. Methylisothiazolone was added as a preservative to a final concentration as needed (approximately 3 ppm) during heating. Approximately 3 minutes after addition of the preservative, the heat is turned off and the mixture is allowed to cool to room temperature. The particles are then transferred to a storage container and analyzed over several days for size, dispersion, color, settlement, and agglomeration. Again, for this product the particle size distribution did not change over a period of several days (as shown by repeated measurements of the product using a Horiba 910 Particle Size Analyzer), thus demonstrating that the particles did not re-agglomerate over time.

Example 5 (Proposed Example)

Antidandruff Shampoo Formulation I

An antidandruff shampoo composition is made using de-agglomerated particles of zinc pyrithione, prepared as described in Examples 1-4, in combination with the following ingredients:

| Component A: | |
|---|---|
| Water | 41.0% |
| Magnesium aluminum silicate | 1.0% |
| Hydroxypropyl methylcellulose | 0.8% |
| Component B: | |
| Zinc Pyrithione (25% aqueous dispersion) | 4.0% |
| Component C: | |
| Cocamide DEA | 1.0% |
| Component D: | |
| Triethanolamine lauryl sulfate, 40% | 40.0% |
| Triethanolamine, 99% | 3.2% |
| FD&C Blue No. 1 (0.2%) | 1.5% |
| FD&C Yellow No. 5 (0.1%) | 0.5% |
| Fragrance | q.s. |

The antidandruff shampoo composition is made as follows:

Component A is prepared by heating water to 70° C. and dissolving the other two components with stirring (about 1500 rpm). Component B is added, and stirring continued for 5 minutes. Stirring speed was reduce stirring to ~300 RPM. Component C is melted in a separate container, and added to the A/B mixture. The heat is removed and component D is added while the mixture cooled.

Example 6 (Proposed Example)

Antidandruff Shampoo Formulation II

Another antidandruff shampoo composition is made using zinc pyrithione made as described in Examples 1-4 in combination with the following ingredients:

| Component A: | |
|---|---|
| Deionized water | q.s. |
| Ammonium lauryl sulfate | 15.0% |
| Cocamide DEA | 2.0% |
| Component B: | |
| Di (hydrogenated) tallow phthalic acid amide | 5.0% |
| Zinc Pyrithione (25% aqueous dispersion) | 4.0% |
| Component C: | |
| Preservative | q.s. |
| Component D: | |
| Citric Acid, 50% aq. Solution, OR Sodium hydroxide, 50% aqueous solution | q.s. |
| Component E: | |
| Ammonium chloride | q.s. |

The antidandruff shampoo composition is made as follows:

In separate containers, components A and B are each mixed well. Component A is heated to 165-170° F. and component B is added. The mixture is stirred for 30 minutes. The mixture is then cooled to 120° F., and component C was added. The pH of the resulting mixture is adjusted to 5.0-6.2 with component D, and the viscosity is adjusted with component E.

Example 7 (Proposed Example)

Antidandruff Shampoo with Conditioner I

An antidandruff shampoo and conditioner composition is made using needle and rod forms of zinc pyrithione made as described in Examples 1-4 in combination with the following ingredients:

| Component A: | |
|---|---|
| Deionized Water | q.s. |
| Ammonium lauryl sulfate | 20.0% |
| Cocamide DEA | 2.0% |
| Component B: | |
| Di (hydrogenated) tallow phthalic acid amide | 4.0% |
| Zinc Pyrithione (25% aqueous dispersion) | 4.0% |
| Dimethicone, 12,000 cps | 0.5% |
| Component C: | |
| Preservative | q.s. |
| Component D: | |
| Citric acid, 50% aqueous solution, OR Sodium hydroxide, 50% aqueous solution | q.s. |
| Component E: | |
| Ammonium chloride | q.s. |

The antidandruff shampoo and conditioner composition is made as follows:

In separate containers, components A and B is each mixed well. Component A is heated to 165-170° F. and component B is added. The mixture is stirred for 30 minutes. The mixture is then cooled to 120° F., and component C was added. The pH of the resulting mixture is adjusted to 5.0-6.2 with component D, and the viscosity is adjusted with component E.

Example 8 (Proposed Example)

Antidandruff Shampoo with Conditioner II

Another antidandruff shampoo and conditioner composition is made using needle and rod forms of zinc pyrithione made as described in Examples 1-4 in combination with the following ingredients:

| Component A: | |
|---|---|
| Deionized water | q.s. |
| Guar hydroxypropyl trimonium chloride | 0.30% |
| Magnesium Aluminum Silicate | 0.70% |
| Zinc Pyrithione (25% aqueous dispersion) | 4.0% |
| Component B: | |
| Sodium laureth sulfate | 30.0% |
| Ammonium xylene sulfonate, 40% aq. | 02.0% |
| Component C: | |
| Tricetylammonium chloride | 0.50% |
| Cetyl alcohol NF | 0.40% |

| -continued | |
|---|---|
| Stearyl alcohol | 0.40% |
| Glycol distearate | 2.00% |
| Component D: | |
| Cocamide MEA | 1.70% |
| Ammonium lauryl sulfate | 36.00% |
| Component E: | |
| Preservative | 0.05% |
| Fragrance and dye | q.s. |
| Component F | |
| Citric acid, 25% aqueous solution | q.s. |

The antidandruff shampoo and conditioner composition is made as follows:

Component A is prepared by heating water to 50° C. and dispersing the guar hydroxypropyl trimonium chloride and the magnesium aluminum silicate with rapid agitation. The zinc pyrithione dispersion is added to this combination with stirring. The pH of component A is adjusted to 4.5-5.0 with component F. Both components of B are slowly added to component A, mixing well. The pH of the mixture is adjusted to 5.7-6.3 with component F. In a separate container, component C is heated to 70-75° C. The A/B mixture is heated to 70-75° C. and blend with component C, mixing well. Both components of D are added to the hot mixture, and stirred well. The pH of the mixture are adjusted to 5.7-6.3 with component F. The mixture is cooled to 40-45° C., and component E was added with stirring. If a higher viscosity is desired, adding 0.05-1% sodium chloride can increase the viscosity of the product.

Example 9 (Proposed Example)

"Extra Body" Antidandruff Shampoo

An "extra body" antidandruff shampoo and conditioner composition is made using needle and rod forms of zinc pyrithione made as described in Examples 1-4 in combination with the following ingredients:

| Component A: | |
|---|---|
| Deionized Water | q.s. |
| Zinc Pyrithione (25% aqueous dispersion) | 4.0% |
| Component B: | |
| Methyl Paraben | 0.30% |
| Propyl Paraben | 0.10% |
| Propylene Glycol | 0.50% |
| Sodium Chloride | 0.50% |
| Component C: | |
| Triethanolamine lauryl sulfate | 20.0% |
| Cocamide MEA | 4.0% |
| Ethylene glycol distearate | 7.0% |
| Component D: | |
| Cocodimonium hydrolyzed animal protein | 1.00% |
| Component E: | |
| FD&C Blue No. 1 | q.s. |
| Component F: | |
| Citric Acid, 50% aqueous solution | q.s. |

The antidandruff shampoo and conditioner composition are made as follows:

Component A is heated to 70° C. The ingredients of component B are added with good stirring until dissolved. The ingredients of component C are added to the mixture sequentially, and heated with mixing to 75° C. The mixture is cooled with stirring to 40° C., and components D and E are added with stirring. The pH of the final composition is adjusted to 4.7 with component F.

Although the invention has been shown and described with respect to illustrative embodiments thereof, it should be appreciated that the foregoing and various other changes, omissions and additions in the form and detail thereof may be made without departing from the spirit and scope of the invention as delineated in the claims. All patents and patent applications mentioned are herein incorporated by reference in their entireties.

What is claimed is:

1. A method for producing a suspension, emulsion, or dispersion of de-agglomerated particles of pyrithione salts, comprising contacting agglomerated pyrithione salt particles with an de-agglomerating agent, in the presence of sonic energy, to produce said suspension, emulsion, or dispersion of de-agglomerated particles of pyrithione salts,
    wherein said de-agglomerating agent is an electrolyte, alone or in combination with an agent selected from the group consisting of surfactants, dispersants, and combinations thereof, and,
    wherein said electrolyte is selected from the group consisting of alkali metal or alkaline earth metal salts, alkali metal or alkaline earth metal oxides, alkali metal or alkaline earth metal hydroxides, zinc chloride, zinc oxide, zinc hydroxide and combinations thereof and
    wherein the de-agglomerated pyrithione salt is chemically identical to that of the agglomerated particles of pyrithione salts.

2. The method of claim 1 wherein said electrolyte is selected from the group consisting of sodium chloride, calcium chloride, zinc chloride, sodium oxide, calcium oxide, zinc oxide, sodium hydroxide, calcium hydroxide, zinc hydroxide, and combinations thereof 3. A method for producing a suspension, emulsion, or dispersion of de-agglomerated particles of pyrithione salts, comprising contacting agglomerated pyrithione salt particles with an de-agglomerating agent in the presence of sonic energy, to produce said suspension, emulsion, or dispersion of de-agglomerated particles of pyrithione salts,
    wherein said de-agglomerating agent is an electrolyte, alone or in combination with an agent selected from the group consisting of surfactants, dispersants, and combinations thereof, and
    wherein said electrolyte is present in said suspension, emulsion or dispersion in and amount of from about 0.01 to 10% by weight, based on the total weight of said admixture and
    wherein the de-agglomerated pyrithione salt is chemically identical to that of the agglomerated particles of pyrithione salts.

4. The method of claim 3, wherein said electrolyte is present in said admixture of agglomerated pyrithione salt particles from about 0.1 to 5% by weight, based on the total weight of said admixture.

5. The method of claim 4, wherein said electrolyte is present in said admixture of agglomerated pyrithione salt particles from about 1 to 3% by weight, based on the total weight of said admixture.

6. A method for producing a suspension, emulsion, or dispersion of de-agglomerated particles of pyrithione salts, comprising contacting agglomerated pyrithione salt particles with an de-agglomerating agent, in the presence of sonic energy, to produce said suspension, emulsion, or dispersion of de-agglomerated particles of pyrithione salts, wherein said de-agglomerating agent is an electrolyte, alone or in combination with an agent selected from the group consisting of surfactants, dispersants, and combinations thereof, and wherein said surfactant is selected from the group consisting of salts of anionic surfactants, cationic surfactants, nonionic surfactants, amphoteric surfactants, arid combinations thereof and wherein the de-agglomerated pyrithione salt is chemically identical to that of the agglomerated particles of pyrithione salts.

* * * * *